US009772425B2

(12) United States Patent
Dangfa et al.

(10) Patent No.: US 9,772,425 B2
(45) Date of Patent: Sep. 26, 2017

(54) DISTINGUISHING MUD FILTRATE FROM FORMATION WATER BY MULTI-DOI NMR

(71) Applicant: Schlumberger Technology Corporation, Sugar Land, TX (US)

(72) Inventors: David Nanlung Dangfa, Aberdeen (GB); Ilaria De Santo, Ellon (GB); Iftikhar Khattak, Aberdeen (GB); Harish Baban Datir, Sandnes (NO)

(73) Assignee: SCHLUMBERGER TECHNOLOGIES CORPORATION, Sugar Land, TX (US)

( * ) Notice: Subject to any disclaimer, the term of this patent is extended or adjusted under 35 U.S.C. 154(b) by 1205 days.

(21) Appl. No.: 13/804,333

(22) Filed: Mar. 14, 2013

(65) Prior Publication Data

US 2013/0271127 A1 Oct. 17, 2013

Related U.S. Application Data

(60) Provisional application No. 61/623,720, filed on Apr. 13, 2012.

(51) Int. Cl.
| G01V 3/00 | (2006.01) |
| G01V 3/32 | (2006.01) |
| G01N 24/08 | (2006.01) |

(52) U.S. Cl.
CPC ............. *G01V 3/32* (2013.01); *G01N 24/081* (2013.01)

(58) Field of Classification Search
CPC ...................................................... G01V 3/32
USPC .................................................. 324/303, 306
See application file for complete search history.

(56) References Cited

U.S. PATENT DOCUMENTS

| 5,629,623 | A | 5/1997 | Sezginer et al. |
| 6,232,778 | B1 | 5/2001 | Speier et al. |
| 7,261,168 | B2 | 8/2007 | McGregor et al. |
| 8,115,481 | B2 | 2/2012 | Chen |
| 2004/0027122 | A1* | 2/2004 | Heaton ............... G01V 3/32 324/303 |
| 2004/0104048 | A1 | 6/2004 | Woodburn et al. |
| 2008/0234937 | A1 | 9/2008 | Fang et al. |
| 2009/0179636 | A1* | 7/2009 | Chen .................. G01N 24/081 324/303 |

(Continued)

OTHER PUBLICATIONS

International Search Report and Written Opinion for International Application No. PCT/US2013/035359 dated Jul. 18, 2013.

*Primary Examiner* — Louis Arana
(74) *Attorney, Agent, or Firm* — Michael Dae

(57) ABSTRACT

A nuclear magnetic resonance (NMR) measurement, at two or more depths of investigation, of a subsurface formation containing formation water and a mud filtrate from a water-base mud is obtained, and the mud filtrate is distinguished from the formation water. A NMR logging tool is disposed in a wellbore penetrating the formation containing the mud filtrate and the formation water and NMR measurements at different radial depths of investigation into the formation are made. The mud filtrate is distinguished from the formation water by determining the relative salinities of the mud filtrate and the formation water. The relative salinities are determined by comparing distribution relaxation times across different depths of investigation or by comparing logarithmic mean values across different depths of investigation.

20 Claims, 5 Drawing Sheets

(56) References Cited

U.S. PATENT DOCUMENTS

2009/0292472 A1  11/2009  Montaron

* cited by examiner

DISTINGUISHING MUD FILTRATE FROM FORMATION WATER BY MULTI-DOI NMR

CROSS-REFERENCE TO RELATED APPLICATIONS

This application is a non-provisional application claiming, under 35 U.S.C. §119, priority to and the benefit of U.S. Provisional Application No. 61/623,720, filed Apr. 13, 2012, the disclosure of which is incorporated by reference herein in its entirety.

BACKGROUND OF THE DISCLOSURE

Nuclear magnetic resonance (NMR) tools used for well-logging or downhole fluid characterization measure the response of nuclear spins in formation fluids to applied magnetic fields. Downhole NMR tools typically have a permanent magnet that produces a static magnetic field at a desired test location (e.g., where the fluid is located). The static magnetic field produces a magnetization in the fluid, whereby the magnetization is aligned along the direction of the static field. The magnitude of the induced magnetization is proportional to the magnitude of the static field. A transmitter antenna produces a time-dependent radio frequency magnetic field that has a component perpendicular to the direction of the static field. As will be appreciated, the NMR resonance condition is satisfied when the radio frequency is equal to the Larmor frequency, which is proportional to the magnitude of the static magnetic field. The radio frequency magnetic field produces a torque on the magnetization vector that causes it to rotate about the axis of the applied radio frequency field. The rotation results in the magnetization vector developing a component perpendicular to the direction of the static magnetic field. This causes the magnetization vector to precess around the static field at the Larmor frequency. At resonance between the Larmor and transmitter frequencies, the magnetization is tipped to the transverse plane (i.e., a plane normal to static magnetic field vector). A series of radio frequency pulses are applied to generate spin echoes that are measured with the antenna.

NMR measurements can be used to estimate, among other things, formation porosity. For example, the area under the curve of a T2 distribution for a NMR measurement can be equated to or at least provides an estimate of the NMR-based porosity. The T2 distribution may also resemble the pore size distribution in water-saturated rocks. The raw reported porosity is provided by the ratio of the initial amplitude of the raw decay and the tool response in a water tank. This porosity is independent of the lithology of the rock matrix.

SUMMARY

A nuclear magnetic resonance (NMR) measurement, at two or more depths of investigation, of a subsurface formation containing formation water and a mud filtrate from a water-base mud is obtained, and the mud filtrate is distinguished from the formation water. A NMR logging tool is disposed in a wellbore penetrating the formation containing the mud filtrate and the formation water and NMR measurements at different radial depths of investigation into the formation are made. The mud filtrate is distinguished from the formation water by determining the relative salinities of the mud filtrate and the formation water. The relative salinities are determined by comparing distribution relaxation times across different depths of investigation or by comparing logarithmic mean values across different depths of investigation.

This summary is provided to introduce a selection of concepts that are further described below in the detailed description. This summary is not intended to identify key or essential features of the claimed subject matter, nor is it intended to be used as an aid in limiting the scope of the claimed subject matter.

BRIEF DESCRIPTION OF THE DRAWINGS

The present disclosure is best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. Embodiments of distinguishing mud filtrate from formation water using multi-DOI NMR logs are described with reference to the following figures. The same numbers are generally used throughout the figures to reference like features and components.

DETAILED DESCRIPTION

Figure 1:
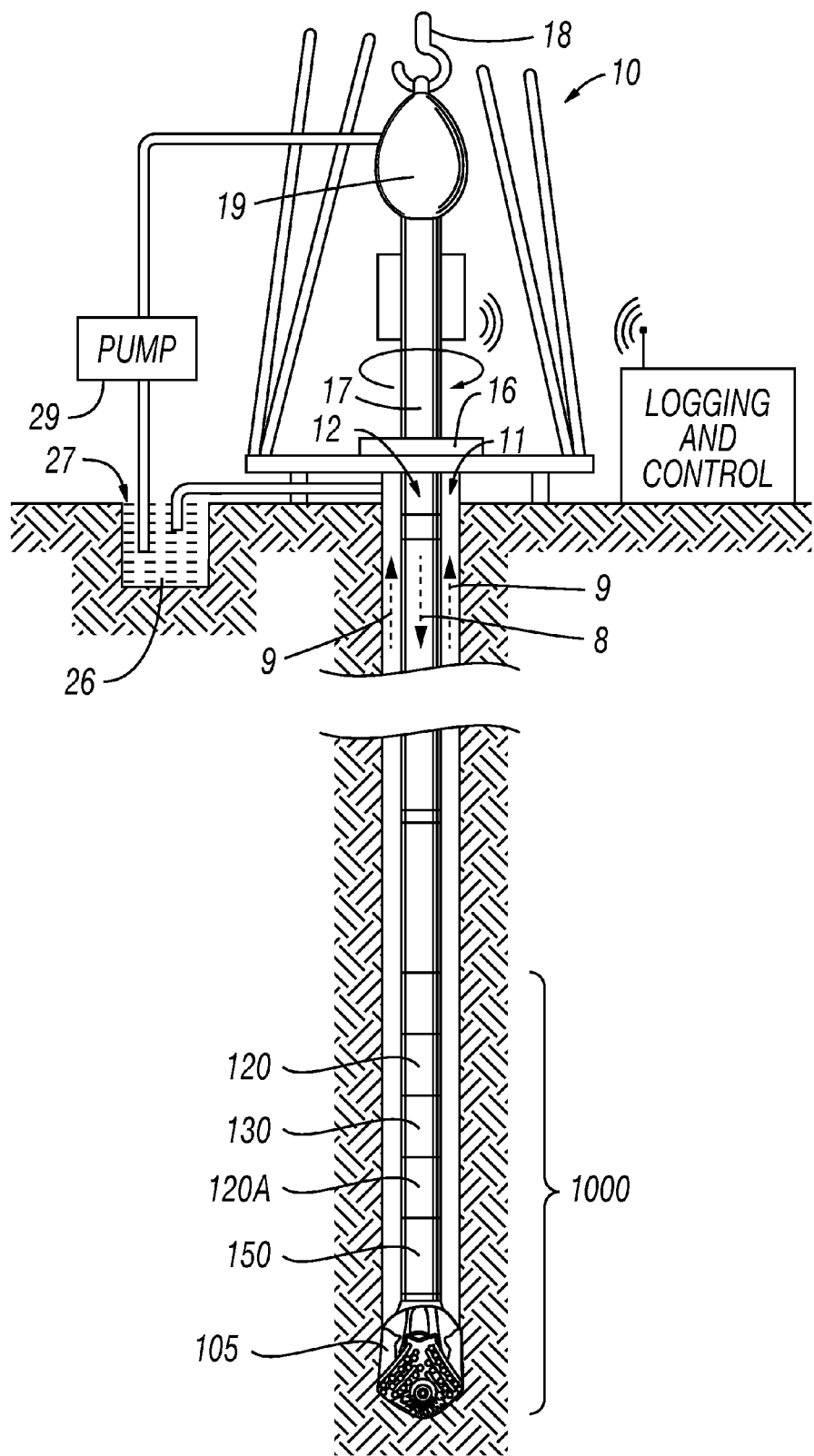
FIG. 1 illustrates an exemplary, prior art well site system.

It is to be understood that the following disclosure provides many different embodiments, or examples, for implementing different features of various embodiments. Specific examples of components and arrangements are described below to simplify the present disclosure. These are, of course, merely examples and are not intended to be limiting. In addition, the present disclosure may repeat reference numerals and/or letters in the various examples. This repetition is for the purpose of simplicity and clarity and does not in itself dictate a relationship between the various embodiments and/or configurations discussed. Moreover, the formation of a first feature over or on a second feature in the description that follows may include embodiments in which the first and second features are formed in direct contact, and may also include embodiments in which additional features may be formed interposing the first and second features, such that the first and second features may not be in direct contact.

FIG. 1 illustrates a well site system in which various embodiments can be employed. The well site can be onshore or offshore. In this exemplary system, a borehole 11 is formed in subsurface formations by rotary drilling in a manner that is well known. Some embodiments can also use directional drilling, as will be described hereinafter.

A drill string 12 is suspended within the borehole 11 and has a bottom hole assembly 1000 which includes a drill bit 105 at its lower end. The surface system includes platform and derrick assembly 10 positioned over the borehole 11, the assembly 10 including a rotary table 16, kelly 17, hook 18 and rotary swivel 19. The drill string 12 is rotated by the rotary table 16, energized by means not shown, which engages the kelly 17 at the upper end of the drill string. The drill string 12 is suspended from a hook 18, attached to a traveling block (also not shown), through the kelly 17 and a rotary swivel 19 which permits rotation of the drill string relative to the hook. As is well known, a top drive system could alternatively be used.

In the example of this embodiment, the surface system further includes drilling fluid or mud 26 stored in a pit 27 formed at the well site. A pump 29 delivers the drilling fluid 26 to the interior of the drill string 12 via a port in the swivel 19, causing the drilling fluid to flow downwardly through the drill string 12 as indicated by the directional arrow 8. The drilling fluid exits the drill string 12 via ports in the drill bit 105, and then circulates upwardly through the annulus region between the outside of the drill string and the wall of the borehole, as indicated by the directional arrows 9. In this manner, the drilling fluid lubricates the drill bit 105 and carries formation cuttings up to the surface as it is returned to the pit 27 for recirculation.

The bottom hole assembly 1000 of the illustrated embodiment includes a logging-while-drilling (LWD) module 120, a measuring-while-drilling (MWD) module 130, a rotary-steerable system and motor 150, and drill bit 105.

The LWD module 120 is housed in a special type of drill collar, as is known in the art, and can contain one or a plurality of known types of logging tools. It will also be understood that more than one LWD and/or MWD module can be employed, e.g., as represented at 120A. (References, throughout, to a module at the position of 120 can alternatively mean a module at the position of 120A as well.) The LWD module includes capabilities for measuring, processing, and storing information, as well as for communicating with the surface equipment. In the present embodiment, the LWD module includes a NMR measuring device.

The MWD module 130 is also housed in a special type of drill collar, as is known in the art, and can contain one or more devices for measuring characteristics of the drill string and drill bit. The MWD tool further includes an apparatus (not shown) for generating electrical power to the downhole system. This may typically include a mud turbine generator powered by the flow of the drilling fluid, it being understood that other power and/or battery systems may be employed. In the present embodiment, the MWD module includes one or more of the following types of measuring devices: a weight-on-bit measuring device, a torque measuring device, a vibration measuring device, a shock measuring device, a stick/slip measuring device, a direction measuring device, and an inclination measuring device.

Figure 2:
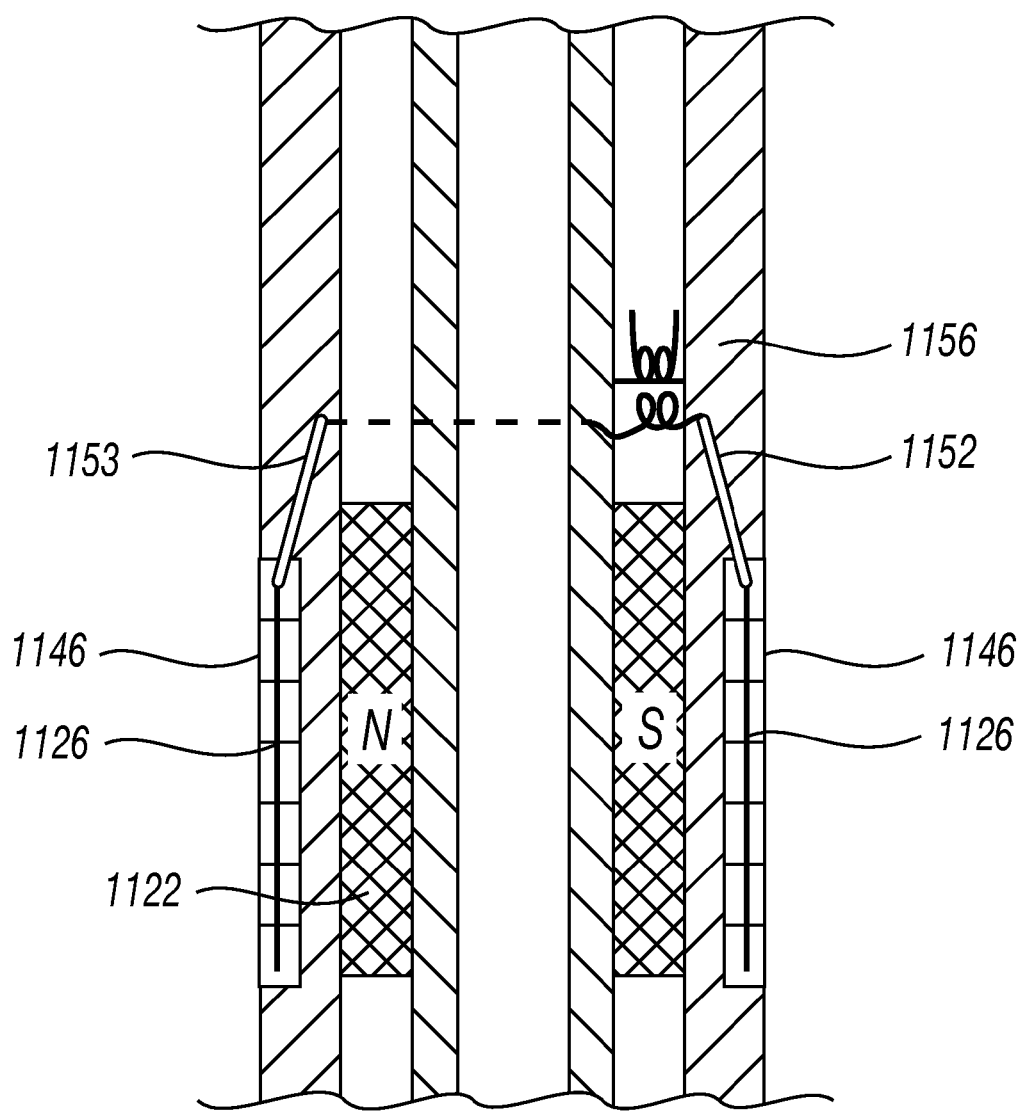
FIG. 2 shows a prior art nuclear magnetic resonance logging tool.

FIG. 2 shows an embodiment of a type of device described in commonly owned U.S. Pat. No. 5,629,623 for formation evaluation while drilling using pulsed nuclear magnetic resonance (NMR), incorporated herein by reference, it being understood that other types of NMR/LWD tools can also be utilized as the LWD tool 120 or part of an LWD tool suite 120A. As described in the '623 Patent, an embodiment of one configuration of the device comprises a modified drill collar having an axial groove or slot that is filled with a ceramic insulator, and contains RF antenna 1126, which is protected by a non-magnetic cover 1146 and produces and receives pulsed RF electromagnetic energy. In the embodiment shown, the conductors of the RF antenna are grounded at one end to the drill collar. At the other end, the conductors are coupled to an RF transformer 1156 via pressure feed-throughs 1152 and 1153. A cylindrical magnet 1122 produces a static magnetic field in the formations. The RF antenna can also be arranged so that the drill collar itself produces the oscillating RF magnetic field. The oscillating RF magnetic field, which excites nuclei of substances in the formations, is axially symmetric, to facilitate measurements during rotation of the drill string.

Although FIGS. 1 and 2 describe the use of a drilling operation and a while-drilling NMR tool, the disclosure herein can relate to any type of NMR tool, whether at the surface or downhole. Moreover, if the NMR tool is a downhole tool, the disclosure herein can apply to the downhole tool regardless of the method of conveyance—e.g., while-drilling, wireline, slickline, coiled tubing, drill pipe conveyance, wired-drill pipe, and the like.

Some embodiments will now be described with reference to the figures. Like elements in the various figures may be referenced with like numbers for consistency. In the following description, numerous details are set forth to provide an understanding of various embodiments and/or features. However, it will be understood by those skilled in the art that some embodiments may be practiced without many of these details and that numerous variations or modifications from the described embodiments are possible. As used here, the terms "above" and "below", "up" and "down", "upper" and "lower", "upwardly" and "downwardly", and other like terms indicating relative positions above or below a given point or element are used in this description to more clearly describe certain embodiments. However, when applied to equipment and methods for use in wells that are deviated or horizontal, such terms may refer to a left to right, right to left, or diagonal relationship, as appropriate.

It will also be understood that, although the terms first, second, etc. may be used herein to describe various elements, these elements should not be limited by these terms. These terms are only used to distinguish one element from another. For example, a first object or step could be termed a second object or step, and, similarly, a second object or step could be termed a first object or step, without departing from the scope of the invention. The first object or step, and the second object or step, are both objects or steps, respectively, but they are not to be considered the same object or step.

The terminology used in the description of the invention herein is for the purpose of describing particular embodiments only and is not intended to be limiting of the invention. As used in the description of the invention and the appended claims, the singular forms "a", "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "includes," "including," "comprises," and/or "comprising," or the like, when used in this specification, specify the presence of stated features, integers, steps, operations, elements, and/or components, but do not preclude the presence or addition of one or more other features, integers, steps, operations, elements, components, and/or groups thereof.

As used herein, the term "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting [the stated condition or event]" or "in response to detecting [the stated condition or event]," depending on the context.

As explained above, when drilling a wellbore, a slurry known as drilling fluid or mud is pumped under pressure downhole through the drill pipe, whereupon it exits through the drill bit and returns through the annulus back to the surface. However, more often than not, some portion of the mud escapes or is lost into the subsurface formation(s). For that mud that escapes into the formation, the particulates suspended in the drilling fluid are filtered out by the rock matrix and accumulate on the wellbore wall, forming what is known as a "filter cake" or "mudcake". The liquid phase of the drilling fluid, however, enters the pores and invades the formation. The liquid phase of the drilling fluid that invades the formation is known as "mud filtrate".

Water is prevalent in many subsurface formations. Most reservoir rocks are formed in water. "Connate water" refers to water trapped in the pores of a rock during its formation, as the sediments compact and bind together. Connate water varies with the depositional environment. In marine sediments, it is seawater. In lake and river deposits, it is freshwater. In evaporate deposits, the interstitial water is high-salinity brine. Thus, the salinity of connate water may vary widely, ranging, for example, from 0.11 parts per thousand (ppk) to 350 ppk.

The water in the reservoir rock at the time the reservoir is penetrated by a drill bit is called "formation water". Formation water, similar to connate water, is also water that occurs naturally within the pores of the rock, and is rich with information about the rock in which it resides. Water from fluids introduced to a formation through drilling or other interference, such as water-base drilling fluid and seawater, does not constitute formation water. Formation water is generally the result of water mixing and other physical and chemical processes, and, like connate water, can also have a wide range of salinities, ranging from approximately 7 ppk to 270 ppk. Those ranges are not absolute, but are provided as being generally representative of connate water and formation water, respectively.

Many, if not most, hydrocarbon-bearing reservoirs have within their pores layers of hydrocarbons and formation water. Each layer is typically in fluid communication with its adjacent layer(s). The water layer is generally the bottom layer, beneath the hydrocarbon layers due to gravitationally-induced separation. Similarly, and for the same reason, the gas layer, if present, usually resides atop the oil layer. Various combinations are possible and often only water and oil or water and gas are present. The different layer boundaries are called the "oil-water contact" (OWC), the "gas-water contact" (GWC), and the "gas-oil contact" (GOC), as appropriate, based on the adjoining layers. The reservoir may therefore be divided conceptually, each layer comprising a particular "leg". That is, there may be a gas leg, an oil leg, and a water leg.

A system and method to distinguish mud filtrate from formation water using multiple depths of investigation NMR (or multi-DOI NMR) logs are disclosed. The disclosed system and method may be used in conjunction with a computing system as described below.

Figure 3:
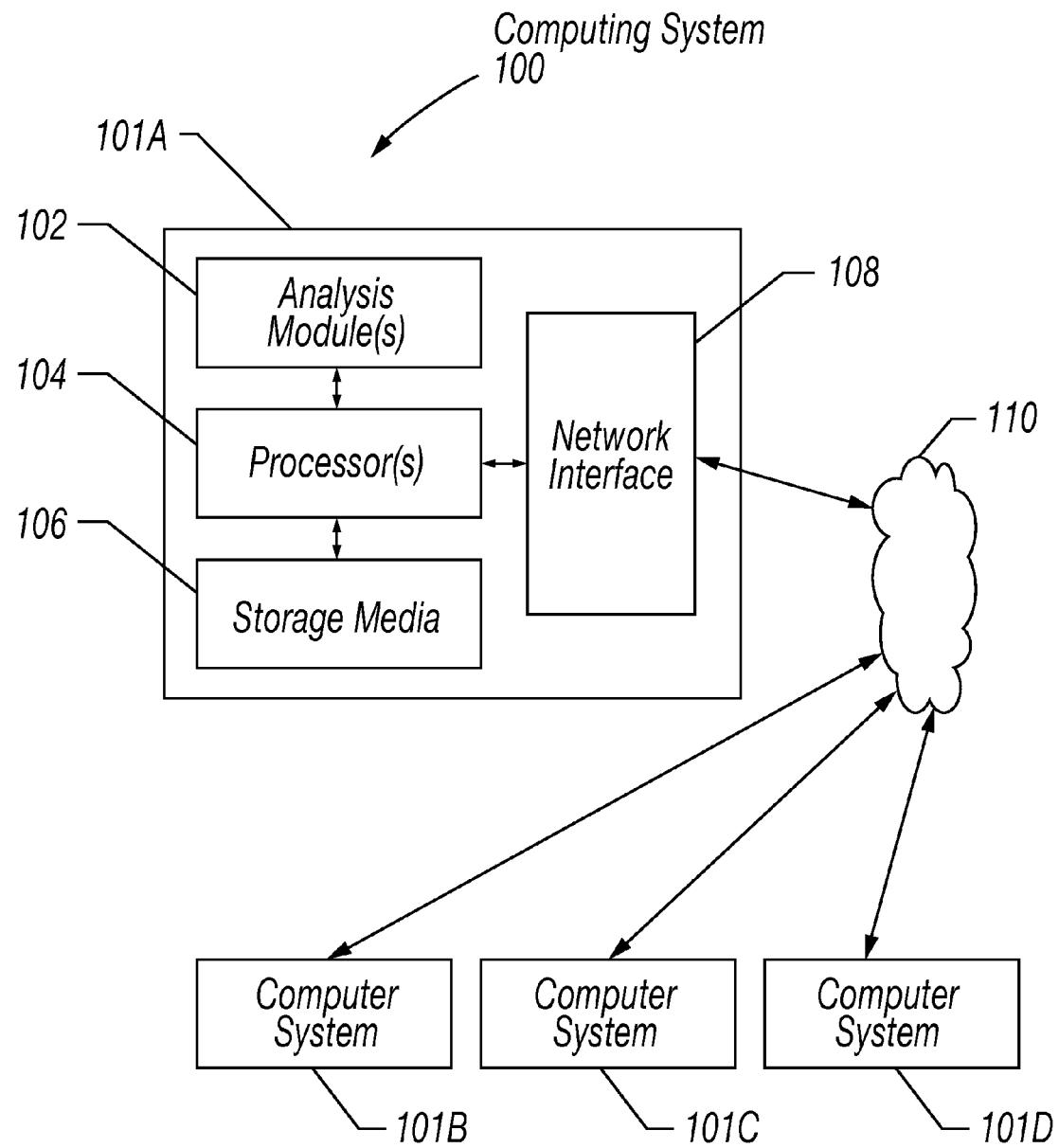
FIG. 3 illustrates an example computing system usable for one or more disclosed embodiments, in accordance with the present disclosure.

The computing system 100 shown in FIG. 3 can be an individual computer system 101A or an arrangement of distributed computer systems. The computer system 101A includes one or more analysis modules 102 that are configured to perform various tasks according to some embodiments, such as one or more methods disclosed herein (e.g., any of the steps, methods, techniques, and/or processes, and/or combinations and/or variations and/or equivalents thereof). To perform those various tasks, analysis module 102 operates independently or in coordination with one or more processors 104 that is (or are) connected to one or more storage media 106. The processor(s) 104 is (or are) also connected to a network interface 108 to allow the computer system 101A to communicate over a data network 110 with one or more additional computer systems and/or computing systems, such as 101B, 101C, and/or 101D (note that computer systems 101B, 101C, and/or 101D may or may not share the same architecture as computer system 101A, and may be located in different physical locations, e.g. computer systems 101A and 101B may be on a ship underway on the ocean, while in communication with one or more computer systems such as 101C and/or 101D that are located in one or more data centers onshore, on other ships, and/or located in various countries on different continents).

A processor can include a microprocessor, microcontroller, processor module or subsystem, programmable integrated circuit, programmable gate array, an ASIC (application specific integrated circuit), an FPGA (field gate programmable array), an SoC (system-on-a-chip) or any another suitable type of control or computing device.

The storage media 106 can be implemented as one or more computer-readable or machine-readable storage media. Note that while in the example embodiment of FIG. 3 storage media 106 is depicted as within computer system 101A, in some embodiments, storage media 106 may be distributed within and/or across multiple internal and/or external enclosures of computing system 101A and/or additional computing systems. Storage media 106 may include one or more different forms of memory including semiconductor memory devices such as dynamic or static random access memories (DRAMs or SRAMs), erasable and programmable read-only memories (EPROMs), electrically erasable and programmable read-only memories (EEPROMs) and flash memories; magnetic disks such as fixed, floppy and removable disks; other magnetic media including tape; optical media such as compact disks (CDs) or digital video disks (DVDs); or other types of storage devices. Note that the instructions discussed above can be provided on one computer-readable or machine-readable storage medium, or alternatively, can be provided on multiple computer-readable or machine-readable storage media distributed in a large system having possibly plural nodes. Such computer-readable or machine-readable storage medium or media is (are) considered to be part of an article (or article of manufacture). An article or article of manufacture can refer to any manufactured single component or multiple components. The storage medium or media can be located either in the machine running the machine-readable instructions, or located at a remote site from which machine-readable instructions can be downloaded over a network for execution.

It should be appreciated that computing system 100 is only one example of a computing system, and that computing system 100 may have more or fewer components than shown, may combine additional components not depicted in the example embodiment of FIG. 3, and/or computing system 100 may have a different configuration or arrangement of the components depicted in FIG. 3. For example, though not shown explicitly, computing system 100 would generally include input and output devices such as a keyboard, a mouse, a display monitor, and a printer and/or plotter. The various components shown in FIG. 3 may be implemented in hardware, software, or a combination of both hardware and software, including one or more signal processing and/or application specific integrated circuits.

Further, the steps in the processing methods described above may be implemented by running one or more functional modules in information processing apparatus such as general purpose processors or application specific chips, such as ASICs, FPGAs, PLDs, or other appropriate devices. These modules, combinations of these modules, and/or their combination with general hardware are all included within the scope of this disclosure.

In operation, a wellbore is logged, either while or after drilling the wellbore. A NMR tool is used to make and record NMR measurements (logs) of the formation surrounding the wellbore at various wellbore depths. The NMR measurements include at least two different depths of investigation. Obtaining NMR measurements at multiple depths of investigation can be achieved by a variety of methods. For example, a tool having one or more antennas capable of operating at multiple frequencies can provide multiple depths of investigation for the NMR measurements. Specifically, the tool may have a main antenna that operates at three frequencies. Those different frequencies correspond to independent measurement volumes (shells) in the form of concentric arcs in front of the antenna. The depths of investigation typically range from 1.5 to 4 inches, but are not limited to that range.

The measured quantities may include the T1 distribution (longitudinal relaxation time), the T2 distribution (transverse relaxation time), or both. The logarithmic mean of a distribution is also a useful computed parameter, determined from the distribution itself. Thus, for a given depth in the wellbore, multiple distributions are measured that correspond to particular shells located at various radial distances away from the tool. Depending on the tool depth in the wellbore, this may be, for example, in the oil leg or the water leg. If the tool is making multi-depth NMR measurements in the water leg, properties of the formation water may be inferred. In particular, the relative salinities of the fluids in the volumes of investigation can be determined. Those fluids (when in the water leg) generally comprise mud filtrate and formation water.

Specifically, if the relaxation times and logarithmic mean values across different depths of investigation are compared, and it is found that the relaxation times and logarithmic mean values increase progressively from the shallowest depth of investigation to the deepest depth of investigation, then one may infer the formation water is less saline than the mud filtrate. Conversely, if the formation water is more saline than the mud filtrate, then relaxation times and log mean values will decrease progressively as one moves farther away (radially outward) from the wellbore.

Various considerations may improve the data measurement quality and interpretability. For example, the NMR logging pulse sequences may be designed or modified, as appropriate, based on known or estimated mud and formation properties. A gradient-field design may be used for data acquisition. The data quality may be evaluated and, if necessary or preferable, the data, particularly older, existing data may be processed or re-processed.

Attention is now directed to processing procedures, methods, techniques, and workflows that are in accordance with some embodiments. Some operations in the processing procedures, methods, techniques, and workflows disclosed herein may be combined and/or the order of some operations may be changed. It is important to recognize that geologic interpretations, sets of assumptions, and/or domain models such as velocity models may be refined in an iterative fashion. This concept is applicable to the processing procedures, methods, techniques, and workflows discussed herein. This iterative refinement can include use of feedback loops executed on an algorithmic basis, such as at a computing device (e.g., computing system 100, FIG. 3), and/or through manual control by a user who may make determinations regarding whether a given step, action, template, or model has become sufficiently accurate for the evaluation of the subsurface three-dimensional geologic formation under consideration.

Figure 4:
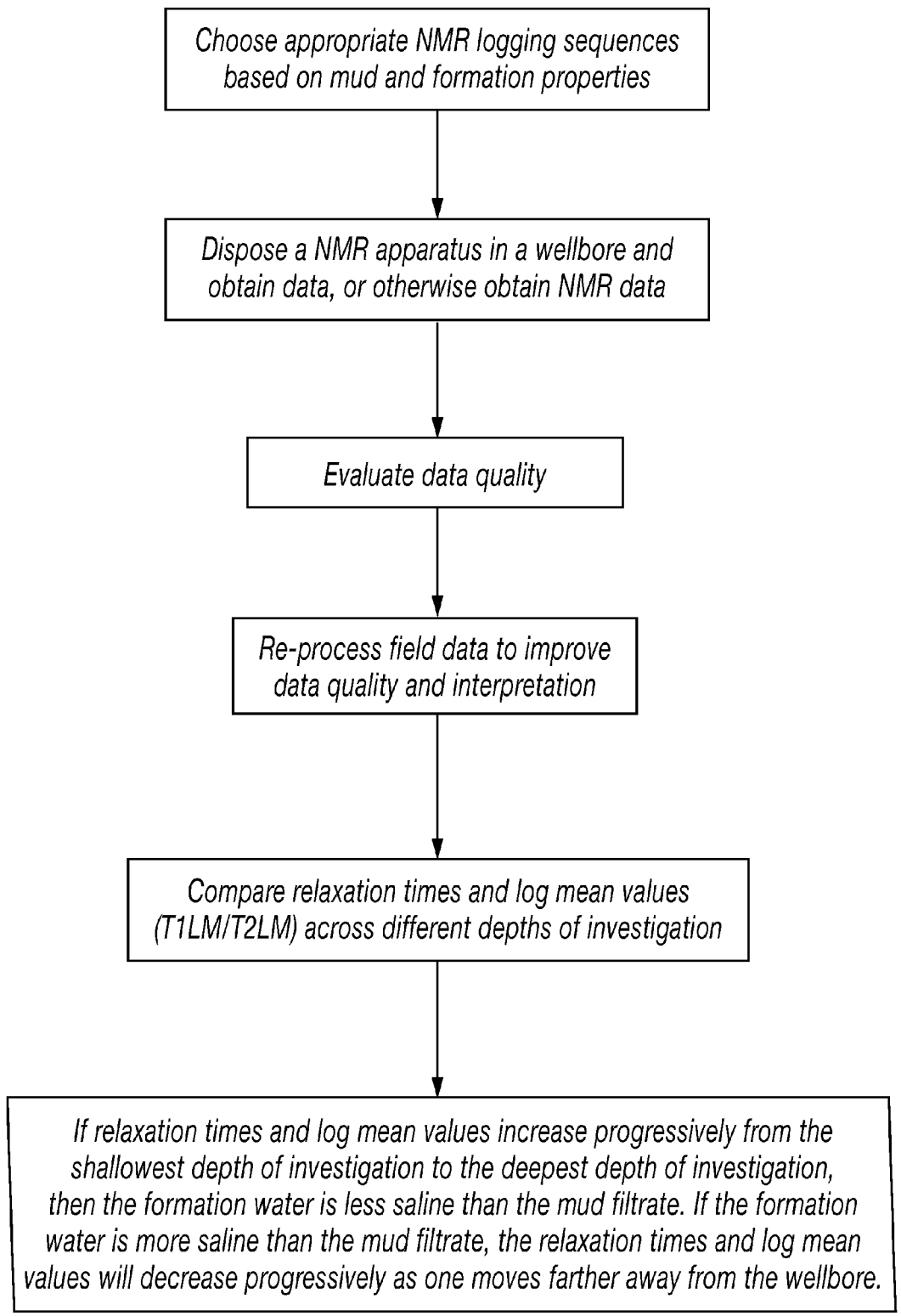
FIG. 4 is a flowchart showing possible steps for one or more embodiments, in accordance with the present disclosure.

FIG. 4 shows a flowchart illustrating an embodiment in accordance with this disclosure. Appropriate NMR logging sequences may be chosen based on mud and formation properties (step 402). A typical acquisition program will include both radial profile and saturation profile modes to take advantage of the multiple depths of investigation of the NMR logging tool. A NMR apparatus may be disposed in a wellbore and data obtained, or NMR data may be otherwise obtained (step 404). The data quality may be evaluated (step 406). For example, system gain, antenna quality factor (AQF), signal phase, tool and environmental noise, tool ringing, echo trend, and comparison of measured porosity with other porosity measurements may be used to evaluate the data quality. If desired, field data may be re-processed to improve data quality and interpretation (step 408). The re-processing may include data stacking, noise filtering, regularization, re-characterizing reservoir fluid properties and map parameters, and re-assigning T1 and T2 cut offs. Relaxation times and log mean values (T1LM/T2LM) may be compared across the different depths of investigation (step 410). If the relaxation times and log mean values increase progressively from the shallowest depth of investigation to the deepest depth of investigation (i.e., as you go farther away from the wellbore), then one may conclude the formation water is less saline than the mud filtrate (step 412). The reverse is the case if the formation water is more saline than the mud filtrate. Relaxation times and log mean values will decrease progressively farther away from the well bore.

Figure 5:
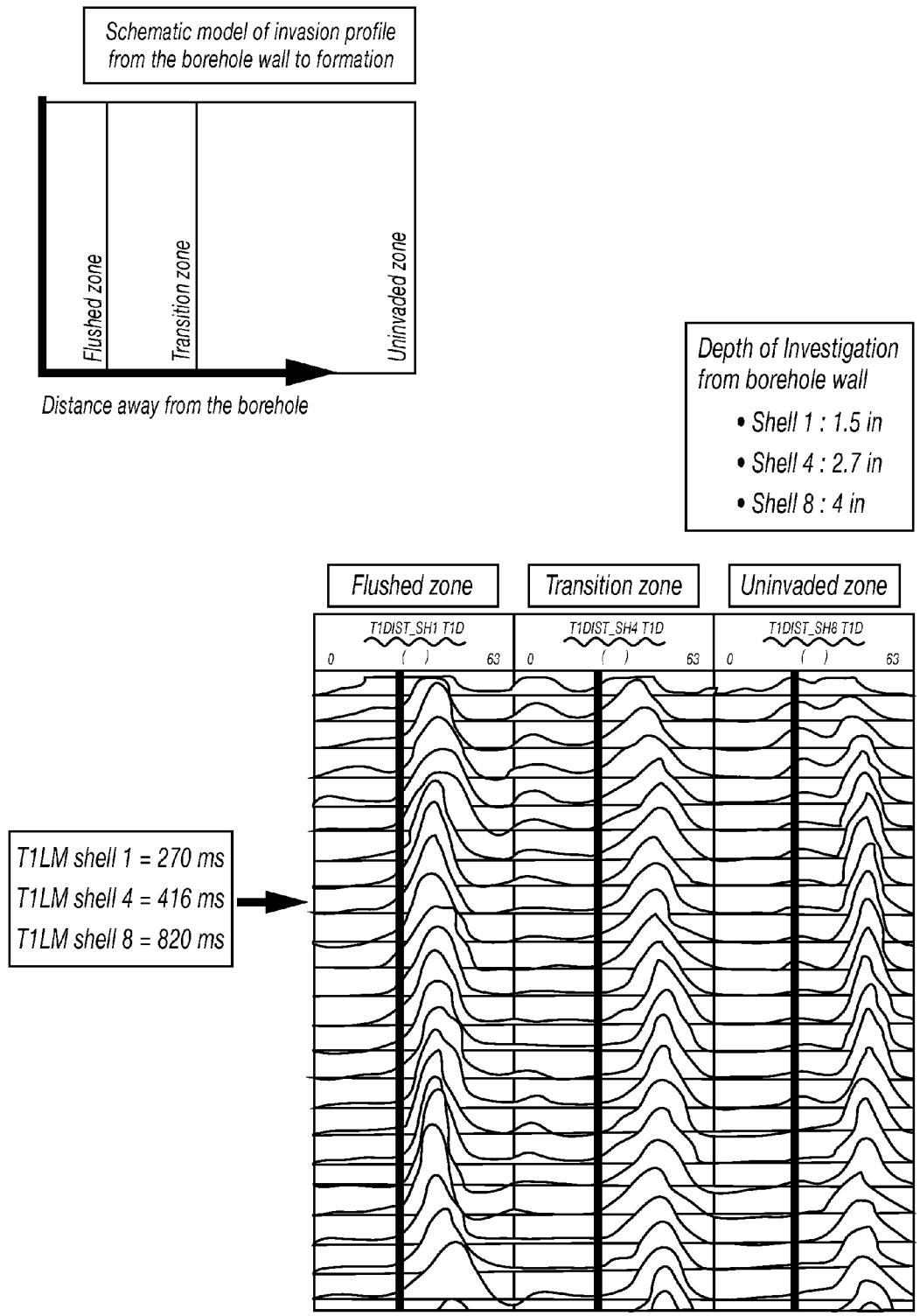
FIG. 5 is a plot showing various NMR measurements (T1 distributions) at various depths of investigation, in accordance with the present disclosure.

FIG. 5 shows an example of various NMR measurements (T1 distributions) at three depths of investigation in the water leg. In this particular embodiment, the three shells are identified as shells 1, 4, and 8. Shell 1 is 1.5 inches away from the wellbore wall, shell 4 is 2.7 inches, and shell 8 is 4 inches. FIG. 5 also includes a schematic model of an invasion profile from the wellbore wall out to the formation. As one moves away from the borehole, one would typically first encounter a region known as the flushed zone, which has significant invasion by the water filtrate. The next zone is a transition zone, which is a mixture of mud filtrate and formation water. Finally, for this example, one would encounter the virgin or uninvaded zone, which contains formation water.

In this example, shell 1 is associated with the flushed zone. The logarithmic mean for the T1 distributions in shell 1 is 270 milliseconds (ms). Shell 4 is associated with the transition zone, and the logarithmic mean for the T1 distributions in shell 4 is 416 ms. Shell 8 is associated with the uninvaded zone, and the logarithmic mean for the T1 distributions in shell 8 is 820 ms. As can be seen from the T1 distributions themselves and from their respective logarithmic means, the relaxation times are progressively increasing as one goes from the shallowest shell to the more distant shells. Thus, one may conclude the formation water is less saline than the mud filtrate.

It is to be noted that NMR well-logging tools differ from those commonly used in the medical field in many respects. Obviously the operating environment for a downhole tool is much harsher than the laboratory setting of an imaging facility. In addition, a downhole NMR is configured "inside-out" relative to a typical "closed" medical NMR device.

That is, medical devices usually look inward to their targeted area, whereas downhole NMR devices look outward into the surrounding formation.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the scope of the present disclosure, and that they may make various changes, substitutions, and alterations herein without departing from the scope of the present disclosure.

The Abstract at the end of this disclosure is provided to comply with 37 C.F.R. §1.72(b) to allow the reader to quickly ascertain the nature of the technical disclosure. It is submitted with the understanding that it will not be used to interpret or limit the scope or meaning of the claims.

While only certain embodiments have been set forth, alternatives and modifications will be apparent from the above description to those skilled in the art. These and other alternatives are considered equivalents and within the scope of this disclosure and the appended claims. Although only a few example embodiments have been described in detail above, those skilled in the art will readily appreciate that many modifications are possible in the example embodiments without materially departing from this invention. Accordingly, all such modifications are intended to be included within the scope of this disclosure as defined in the following claims. In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C. §112, paragraph 6 for any limitations of any of the claims herein, except for those in which the claim expressly uses the words 'means for' together with an associated function.

What is claimed is:

1. A method, comprising:
   obtaining a nuclear magnetic resonance (NMR) measurement, at two or more depths of investigation, of a subsurface formation containing formation water and a mud filtrate from a water-base mud; and
   distinguishing the mud filtrate from the formation water based on the nuclear magnetic resonance measurements from the two or more depths of investigation.

2. The method of claim 1, wherein obtaining the nuclear magnetic resonance measurement comprises disposing a nuclear magnetic resonance logging tool into a wellbore penetrating the formation containing the mud filtrate and the formation water.

3. The method of claim 2, wherein the nuclear magnetic resonance logging tool is configured to make NMR measurements at different radial depths of investigation into the formation.

4. The method of claim 1, wherein obtaining the nuclear magnetic resonance (NMR) measurement comprises designing or modifying a pulse sequence.

5. The method of claim 1, wherein obtaining the nuclear magnetic resonance (NMR) measurement comprises using a gradient-field design.

6. The method of claim 1, wherein obtaining a nuclear magnetic resonance (NMR) measurement comprises processing or re-processing newly acquired or already existing NMR data.

7. The method of claim 1, wherein distinguishing the mud filtrate from the formation water comprises determining the relative salinities of the mud filtrate and the formation water.

8. The method of claim 1, wherein distinguishing the mud filtrate from the formation water comprises comparing distribution relaxation times across different depths of investigation.

9. The method of claim 1, wherein distinguishing the mud filtrate from the formation water comprises comparing logarithmic mean values across different depths of investigation.

10. A computing system comprising at least one processor, at least one memory, and one or more programs stored in the at least one memory, wherein the programs comprise instructions, which when executed by the at least one processor, are configured to perform:
    obtaining a nuclear magnetic resonance (NMR) measurement, at two or more depths of investigation, of a subsurface formation containing formation water and a mud filtrate from a water-base mud; and
    distinguishing the mud filtrate from the formation water based on the nuclear magnetic resonance measurements from the two or more depths of investigation.

11. The system of claim 10, wherein obtaining the nuclear magnetic resonance measurement comprises disposing a nuclear magnetic resonance logging tool into a wellbore penetrating the formation containing the mud filtrate and the formation water, and wherein the nuclear magnetic resonance logging tool is capable of making NMR measurements at different radial depths of investigation into the formation.

12. The system of claim 10, wherein obtaining the nuclear magnetic resonance (NMR) measurement comprises designing or modifying a pulse sequence.

13. The system of claim 10, wherein obtaining the nuclear magnetic resonance (NMR) measurement comprises using a gradient-field design.

14. The system of claim 10, wherein obtaining the nuclear magnetic resonance (NMR) measurement comprises processing or re-processing newly acquired or already existing NMR data.

15. The system of claim 10, wherein distinguishing the mud filtrate from the formation water comprises determining the relative salinities of the mud filtrate and the formation water.

16. The system of claim 10, wherein distinguishing the mud filtrate from the formation water comprises comparing distribution relaxation times across different depths of investigation.

17. The system of claim 10, wherein distinguishing the mud filtrate from the formation water comprises comparing logarithmic mean values across different depths of investigation.

18. A non-transitory, computer-readable storage medium, which has stored therein one or more programs, the one or more programs comprising instructions, which when executed by a processor, cause the processor to perform a method comprising:
    obtaining a nuclear magnetic resonance (NMR) measurement, at two or more depths of investigation, of a subsurface formation containing formation water and a mud filtrate from a water-base mud and;

distinguishing the mud filtrate from the formation water based on the nuclear magnetic resonance measurements from the two or more depths of investigation.

19. The non-transitory, computer-readable storage medium of claim 18, wherein the distinguishing of the mud filtrate from the formation water comprises comparing distribution relaxation times across different depths of investigation.

20. The non-transitory, computer-readable storage medium of claim 18, wherein the distinguishing of the mud filtrate from the formation water comprises comparing logarithmic mean values across different depths of investigation.

* * * * *